(12) United States Patent
Rathbun et al.

(10) Patent No.: US 9,949,768 B2
(45) Date of Patent: Apr. 24, 2018

(54) TRANSCONNECTOR

(71) Applicant: DePuy Synthes Products, Inc., Raynham, MA (US)

(72) Inventors: David S. Rathbun, Gap, PA (US); Jason Banowetz, Glenside, PA (US); Heather Eames, Lansdale, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/344,952

(22) Filed: Nov. 7, 2016

(65) Prior Publication Data
US 2017/0049486 A1    Feb. 23, 2017

Related U.S. Application Data

(63) Continuation of application No. 13/896,864, filed on May 17, 2013, now Pat. No. 9,510,870, which is a continuation of application No. 13/418,912, filed on Mar. 13, 2012, now Pat. No. 8,454,661, which is a continuation of application No. 12/680,089, filed as application No. PCT/US2008/077471 on Sep. 24, 2008, now Pat. No. 8,262,701.

(60) Provisional application No. 60/975,071, filed on Sep. 25, 2007.

(51) Int. Cl.
*A61B 17/70* (2006.01)
*A61B 17/88* (2006.01)

(52) U.S. Cl.
CPC ...... *A61B 17/7052* (2013.01); *A61B 17/7049* (2013.01); *A61B 17/88* (2013.01); *A61B 17/705* (2013.01)

(58) Field of Classification Search
CPC .............. A61B 17/7049; A61B 17/705; A61B 17/7052
USPC ......................... 606/246, 250–253, 260, 278
See application file for complete search history.

(56) References Cited

U.S. PATENT DOCUMENTS

| | | |
|---|---|---|
| 5,330,473 A | 7/1994 | Howland |
| 5,624,442 A | 4/1997 | Mellinger et al. |
| 5,716,355 A | 2/1998 | Jackson et al. |
| 5,752,954 A | 5/1998 | Mata et al. |

(Continued)

FOREIGN PATENT DOCUMENTS

JP    2007-526007 A    9/2007

*Primary Examiner* — Ellen C Hammond
*Assistant Examiner* — Christina Negrellirodriguez
(74) *Attorney, Agent, or Firm* — Baker & Hostetler LLP

(57) ABSTRACT

A transconnector for use in interconnecting a pair of longitudinal spinal rods in a spinal fixation procedure. The transconnector includes a bridge member and first and second spinal rod engaging members. The bridge member may include first and second members, wherein the first and second members are moveably associated with one another so that the distance between the first and second spinal rod engaging members can be adjusted. The first and second spinal rod engaging members include a rod receiving channel for receiving one of the spinal rods therein. The spinal rod engaging members may be articulating in, for example, the yaw and roll positions or non-articulating with respect to the bridge members. The spinal rod engaging members preferably include a spring, for example, a spring washer, to provide an opposing force so that the spinal rod engaging members can provisionally snap onto the spinal rods.

19 Claims, 12 Drawing Sheets

(56) References Cited

U.S. PATENT DOCUMENTS

| | | |
|---|---|---|
| 5,947,966 A | 9/1999 | Drewry et al. |
| 5,980,523 A | 11/1999 | Jackson |
| 6,015,409 A | 1/2000 | Jackson |
| 6,022,350 A | 2/2000 | Ganem |
| 6,080,153 A | 6/2000 | Mata et al. |
| 6,096,039 A | 8/2000 | Stoltenberg et al. |
| 6,217,578 B1 | 4/2001 | Crozet et al. |
| 6,238,396 B1 | 5/2001 | Lombardo |
| 6,261,288 B1 | 7/2001 | Jackson |
| 6,554,831 B1 | 4/2003 | Rivard et al. |
| 6,602,253 B2 | 8/2003 | Richelsoph et al. |
| 6,616,668 B2 | 9/2003 | Altarac et al. |
| 6,749,612 B1 | 6/2004 | Conchy et al. |
| 6,761,721 B2 | 7/2004 | Burgess et al. |
| 6,872,208 B1 | 3/2005 | McBride et al. |
| 6,887,241 B1 | 5/2005 | McBride et al. |
| 7,066,938 B2 | 6/2006 | Slivka et al. |
| 7,481,827 B2 | 1/2009 | Ryan et al. |
| 7,842,071 B2 * | 11/2010 | Hawkes ............. A61B 17/7052 606/252 |
| 8,226,689 B2 | 7/2012 | Jones et al. |
| 2003/0114853 A1 | 6/2003 | Burgess et al. |
| 2004/0138659 A1 | 7/2004 | Austin et al. |
| 2004/0267264 A1 | 12/2004 | Konieczynski et al. |
| 2005/0090821 A1 | 4/2005 | Berrevoets et al. |
| 2005/0113831 A1 | 5/2005 | Franck et al. |
| 2005/0228377 A1 | 10/2005 | Chao et al. |
| 2006/0058789 A1 | 3/2006 | Kim et al. |
| 2006/0233597 A1 | 10/2006 | Ensign et al. |
| 2007/0135817 A1 | 6/2007 | Ensign |
| 2007/0219556 A1 | 9/2007 | Altarac et al. |

\* cited by examiner

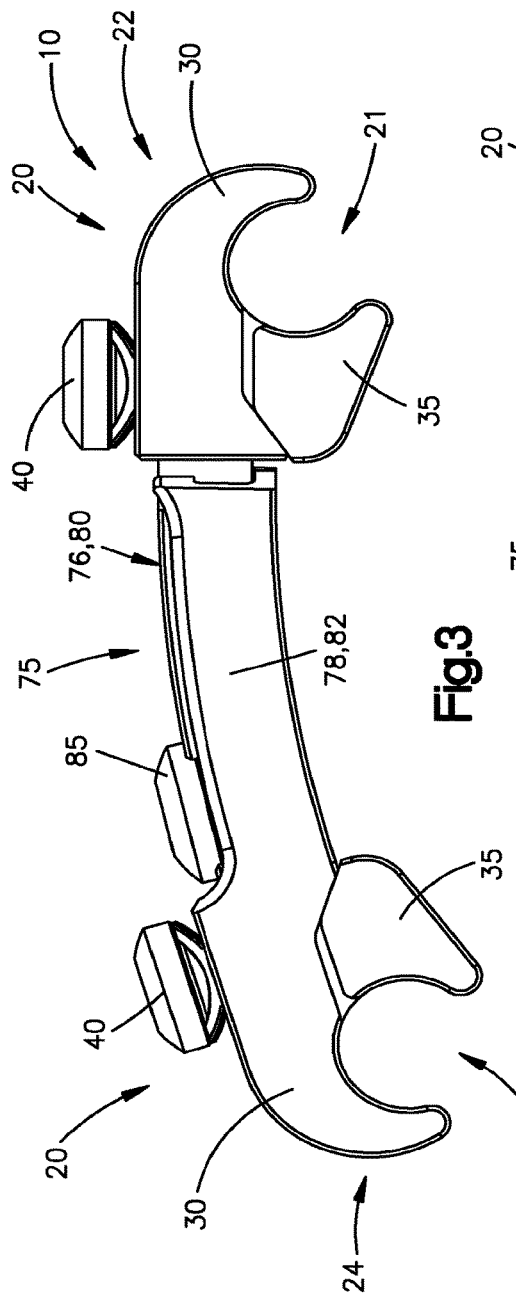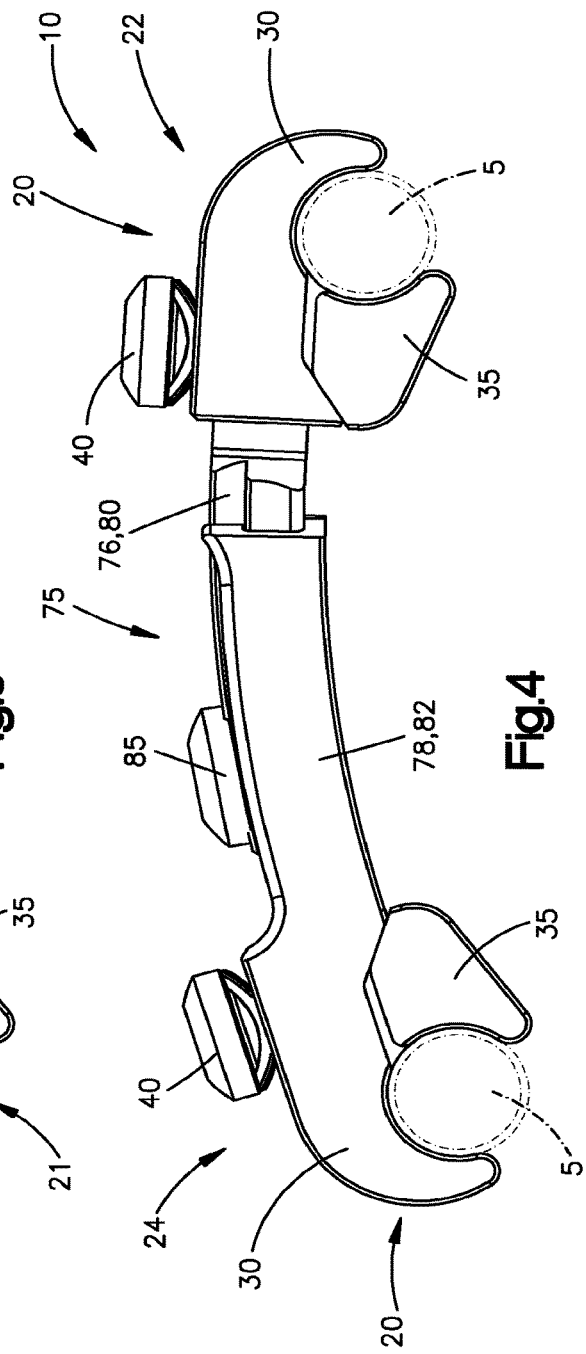

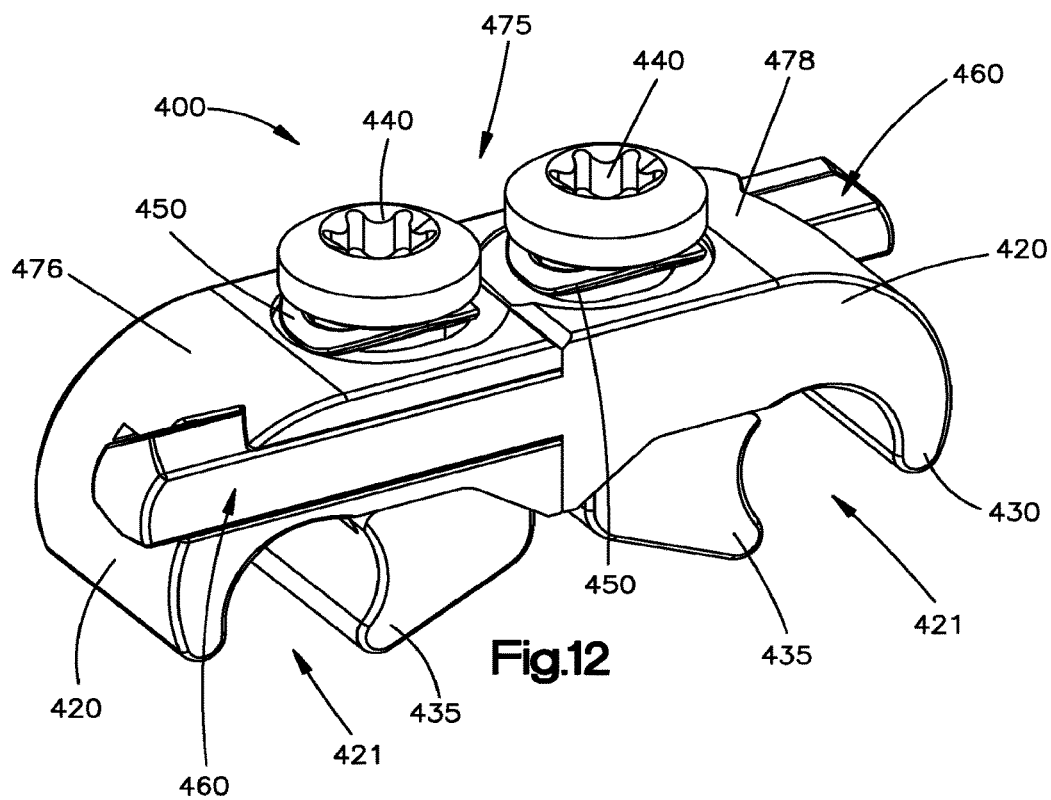
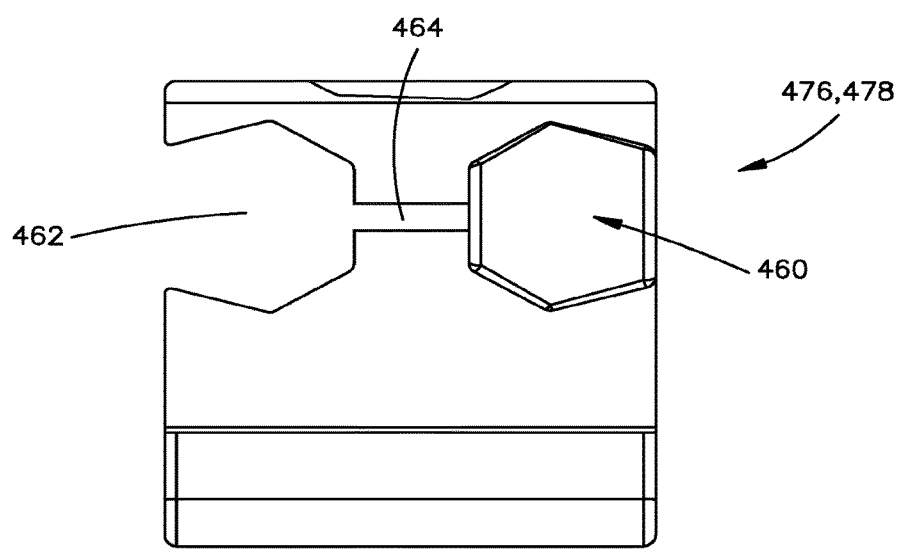

TRANSCONNECTOR

CROSS REFERENCE TO RELATED APPLICATIONS

This application is a continuation of U.S. patent application Ser. No. 13/896,864, filed May 17, 2013, which is a continuation of U.S. patent application Ser. No. 13/418,912, filed Mar. 13, 2012, now U.S. Pat. No. 8,454,661, issued Jun. 4, 2013, which is a continuation of U.S. patent application Ser. No. 12/680,089, filed Mar. 25, 2010, now U.S. Pat. No. 8,262,701, issued Sep. 11, 2012, which is the National Stage Entry of PCT Application No. PCT/US2008/077471, filed Sep. 24, 2008, which claims the benefit of U.S. Provisional Application No. 60/975,071, filed Sep. 25, 2007, each of which are herein incorporated by reference in their entireties.

FIELD OF THE INVENTION

The present invention relates to a device for spinal fixation, and in particular to a transconnector for coupling longitudinal spinal rods, or other elongated members.

BACKGROUND OF THE INVENTION

Spinal fusion is a procedure that involves joining two or more adjacent vertebrae with a spinal fixation device to restrict movement of vertebrae with respect to one another. For a number of known reasons, spinal fixation devices are used in spine surgery to align and/or fix a desired relationship between adjacent vertebrae. Such devices typically include a pair of spinal fixation devices, such as, for example, a longitudinally spinal rod, a plate, etc., longitudinally placed on the posterior spine on either side of the spinous processes of the vertebral column. The spinal fixation devices are coupled to adjacent vertebrae by two or more bone fixation elements, such as, for example, hooks, bolts, wires, screws, etc. Surgeons commonly choose to implant multiple bone fixation elements, as well as multiple spinal fixation devices, to treat a given spinal disorder. The spinal fixation devices may have a predetermined contour and, once implanted, the spinal fixation device may hold the vertebrae in a desired spatial relationship until desired healing or spinal fusion has taken place or for some longer period of time.

It is also known that the strength and stability of dual spinal rod assemblies can be increased by coupling the two spinal rods together with a cross-brace or transconnector, which typically extends substantially transverse to the spinal rods and generally horizontally across the spine to interconnect the longitudinal spinal rods. The use of transconnectors, however, can provide surgeons with one or more difficulties. The simplest situation in which a transconnector could be used occurs when the two spinal rods are substantially parallel to each other, i.e. there is no rod convergence or divergence in the medial-lateral direction; where the two spinal rods have the same orientation with respect to the coronal plane viewed in the anterior-posterior direction, i.e. the spinal rods are coplanar from a lateral view; and where the two spinal rods are located at a fixed, predetermined distance from each other. However, due to a wide variety of factors, the two spinal rods are rarely geometrically aligned in this manner in clinical situations.

Thus, it is advantageous to provide a transconnector which may be adjusted to adapt to variations in spinal rod alignment. The addition of such adjustability, however, may require the transconnector to include numerous pieces that can be difficult to assemble and use while in the surgical environment.

Furthermore, it is advantageous to provide a transconnector with as small a profile as possible to decrease the total amount of soft tissue trauma incurred, and to minimize the chance for subsequent complications. Providing a transconnector with a small profile is also beneficial when attempting to engage longitudinal spinal rods wherein, for one reason or another, the bone fixation elements are closely spaced together.

It is further advantageous to provide a transconnector that, once assembled, prevents disassembly of the individual pieces thereby helping to facilitate implantation of the transconnector by reducing the likelihood that the transconnector will accidentally come apart during implantation in the patient. It is also advantageous to provide a transconnector that reduces the overall number of steps required to fix the location of the transconnector with respect to the longitudinal spinal rods, thereby facilitating implantation of the transconnector by reducing the time and effort needed for implantation in the patient.

Thus, there exists a need for an improved transconnector for coupling adjacent spinal rods which advantageously may be adapted to adjust to varying spinal rod alignments, which has a reduced footprint for reducing associated tissue trauma and, which when pre-assembled, will remain intact during implantation in the patient.

SUMMARY OF THE INVENTION

A preferred embodiment of the present invention is directed to a transconnector for use in interconnecting a pair of longitudinal spinal rods in a posterior spinal fixation procedure. The transconnector may include a bridge member and first and second spinal rod engaging members. The bridge member may include first and second members, wherein the first and second members are moveably associated with one another so that the distance between the first and second spinal rod engaging members can be adjusted. The first and second spinal rod engaging members may include an upper clamp body and a lower clamp body, wherein the upper and lower clamp bodies define a rod receiving channel for receiving one of the spinal rods therein. The spinal rod engaging members may be articulating or non-articulating with respect to the bridge members. The spinal rod engaging members preferably also include a spring, for example, a spring washer, to provide an opposing or biasing force so that the spinal rod engaging members can provisionally snap onto or tentatively engage the spinal rods.

In one exemplary embodiment, the transconnector may include a bridge member having first and second ends and first and second rod engaging members. The first rod engaging member is coupled to the first end of the bridge member while the second rod engaging member is coupled to the second end of the bridge member. The first and second rod engaging members each include a rod receiving channel for receiving first and second rods, respectively. At least the first rod engaging member being able to articulate with respect to the bridge member. The first rod engaging member including an upper clamp body, a lower clamp body, an actuation screw, a compression cap and a spring. The first end of the bridge member including a bore for receiving the actuation screw such that the actuation screw passes through the spring, the compression cap, the upper clamp body, the first end of the bridge member and into threaded engagement with the lower clamp body such that rotation of the actuation screw moves the lower clamp body with respect to the upper clamp body to thereby secure the rod within the rod receiving channel and to secure the position of the first rod engaging member with respect to the bridge member. The spring biasing the lower clamp body into engagement with the upper clamp body so that the first rod engaging member can provisionally snap onto the rod received within the rod receiving channel.

BRIEF DESCRIPTION OF THE DRAWINGS

The foregoing summary, as well as the following detailed description of the preferred embodiments of the application, will be better understood when read in conjunction with the appended drawings. For the purposes of illustrating the preferred transconnectors of the present application, there is shown in the drawings preferred embodiments. It should be understood, however, that the application is not limited to the precise arrangements and instrumentalities shown. In the drawings:

FIG. 3 illustrates a side elevational view of the transconnector of FIG. 1, shown in a collapsed position;

FIG. 4 illustrates a side elevational view of the transconnector of FIG. 1, shown in a partially expanded position;

FIG. 12 illustrates a side perspective view of a transconnector in accordance with a fifth preferred embodiment of the present invention; and FIG. 13 illustrates a front elevational view of a bridge member used in connection with the transconnector of FIG. 12.

DETAILED DESCRIPTION OF THE INVENTION

Figure 1:
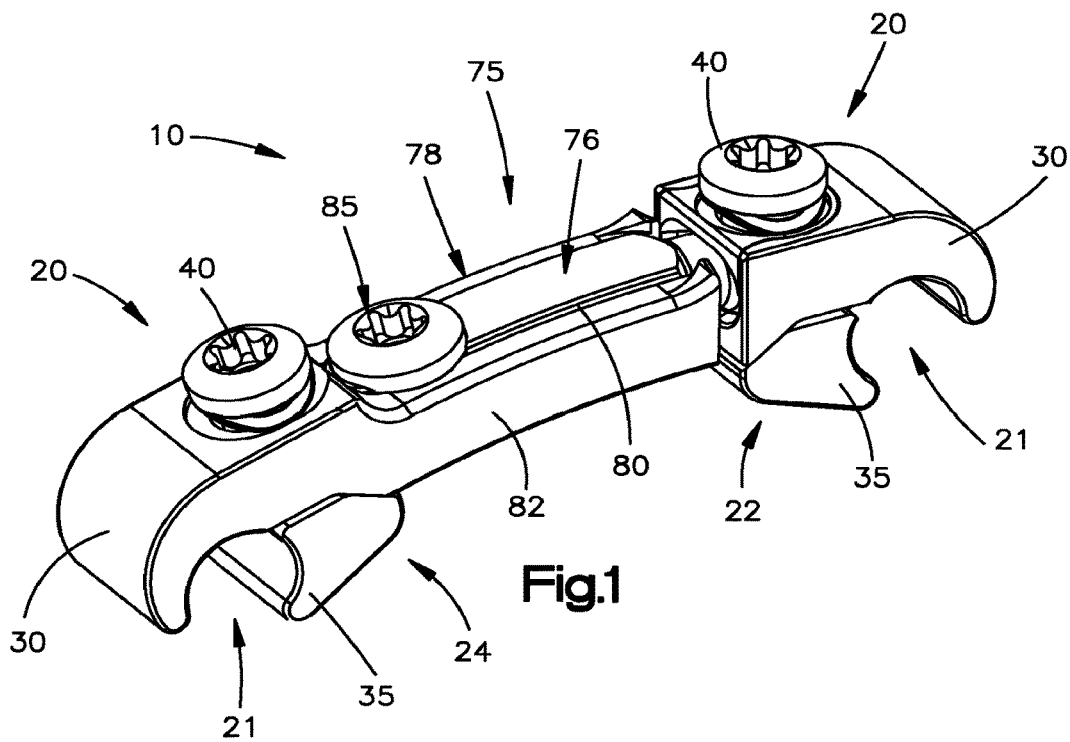
FIG. 1 illustrates a side perspective view of a transconnector in accordance with a first preferred embodiment of the present invention.
Figure 2:
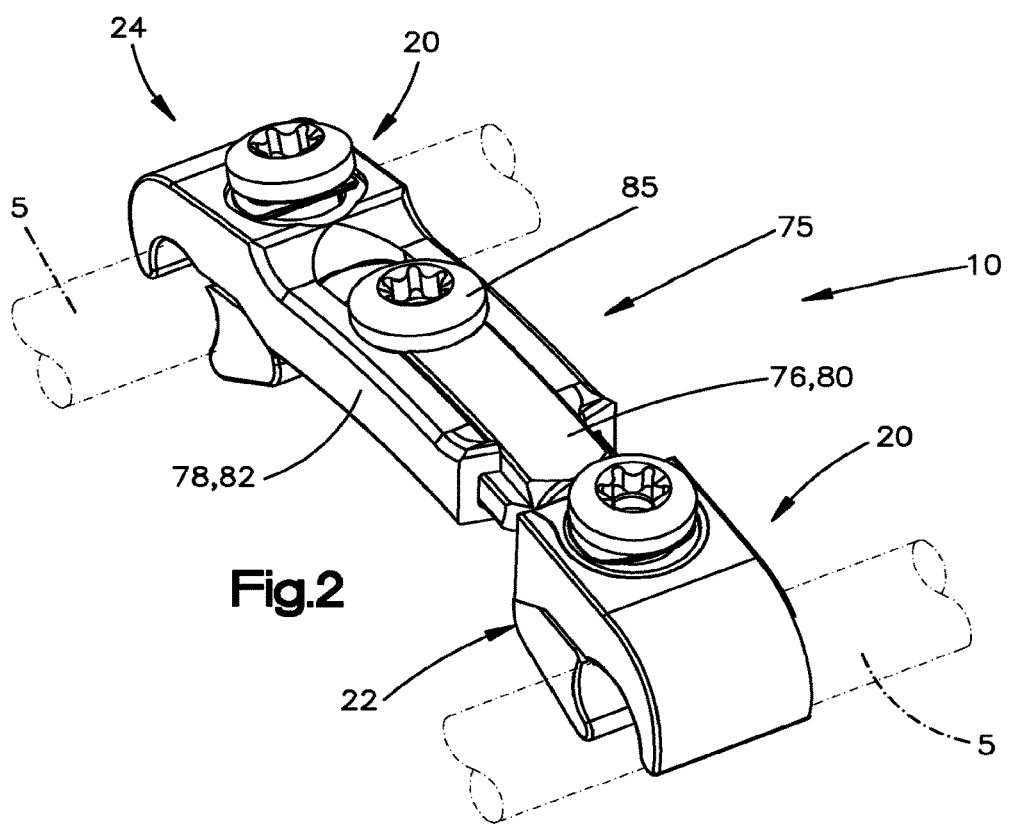
FIG. 2 illustrates a top perspective view of the transconnector of FIG. 1.

Certain terminology is used in the following description for convenience only and is not limiting. The words "right", "left", "top" and "bottom" designate directions in the drawings to which reference is made. The words "inwardly" and "outwardly" refer to directions toward and away from, respectively, the geometric center of the device and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Referring to FIGS. 1-13, certain exemplary embodiments will now be described with reference to the drawings, wherein like reference numerals are used to refer to like elements throughout. In general, such embodiments relate to cross-braces or transconnectors 10, 10', 200, 300, 400 (collectively referred to herein as a transconnector), by way of non-limiting example, the transconnectors 10, 10', 200, 300, 400 are preferably used for interconnecting a pair of longitudinal spinal rods in a posterior spinal fixation procedure. The transconnectors 10, 10', 200, 300, 400 may have other applications and uses and should not be limited to the structure or use described and illustrated. For example, it is envisioned, that the transconnectors 10, 10', 200, 300, 400 may be configured to engage only one spinal rod 5, while another end of the transconnectors 10, 10', 200, 300, 400 is configured to directly engage a patient's vertebra via, for example, a bone screw.

In use, the transconnectors 10, 10', 200, 300, 400 may be configured to provide multiple degrees of freedom to permit the transconnectors 10, 10', 200, 300, 400 to accommodate varying alignments of spinal rods 5. For example, the transconnectors 10, 10', 200, 300, 400 may be configured to angulate and translate with respect to the longitudinal spinal rods 5 after being initially coupled at one end to the spinal rod 5, thus permitting the transconnectors 10, 10', 200, 300, 400 to accommodate, for example, converging and/or diverging longitudinal spinal rods 5, non-coplanar longitudinal spinal rods 5, and longitudinal spinal rods 5 that have varying rod separation distances.

Moreover, while the preferred transconnectors 10, 10', 200, 300, 400 are described as and may generally be used in the spine (for example, in the lumbar, thoracic or cervical regions), those skilled in the art will appreciate that the transconnectors 10, 10', 200, 300, 400 may be used for fixation of other parts of the body such as, for example, joints, long bones or bones in the hand, face, feet, etc. In addition, the transconnectors 10, 10', 200, 300, 400 may be used for external fixation of the body such as, for example, where rods are joined outside of the patient's body to, for example, the patient's vertebra, long bones, etc.

The preferred transconnectors 10, 10', 200, 300, 400 may be constructed from any biocompatible material including, but not limited to, stainless steel, titanium, titanium alloys, polymers, memory shaped alloys, etc. that is able to take on the general shape of the transconnectors 10, 10', 200, 300, 400 and withstand the normal operating conditions of the transconnectors 10, 10', 200, 300, 400.

It should also be understood that the longitudinal spinal rod 5 may include, but not be limited to, a solid rod, a non-solid rod, a flexible or dynamic rod, etc. Alternatively, the longitudinal spinal rod 5 may not be a rod at all and may be in the shape of, for example, a plate. It should be understood that the transconnectors 10, 10', 200, 300, 400 are not limited for use in combination with or as an assembly with any particular type of longitudinal spinal rod 5.

Referring to the first preferred embodiment shown in FIGS. 1-6B, the transconnector 10 may include a pair of spinal rod engaging members 20 and a bridge member 75.

The bridge member 75 preferably includes a first member 76 and a second member 78 wherein the first and second members 76, 78 are moveable displaceable with respect to one another so that the length of the transconnector 10 can be adjusted to vary the distance between the spinal rod engaging members 20 so that the transconnector 10 can accommodate various distances between longitudinal spinal rods 5. By providing an adjustable length bridge member 75, the transconnector 10 is able to allow for varied medial to lateral adjustment. Alternatively, the bridge member 75 may be in the form of a single, nonadjustable fixed length member. In the first preferred embodiment, the first and second members 76, 78 of the bridge member 75 are slidably mounted to each other for movement between a collapsed position (FIG. 3) and an expanded position (not shown). However, the first and second members 76, 78 are not limited to being slidably mounted together and may be alternatively mounted relative to each other to permit modification of the distance and/or orientation of the engaging members 20 relative to each other.

The first and second members 76, 78 may take on any number of forms, including but not limited to, for example, outer and inner telescopic rods wherein the inner rod is telescopically received within the outer telescopic rod. Alternatively, the first and second members 76, 78 may be in the form of lateral side by side members that slide relative to one another to provide an adjustable length bridge member 75. Other arrangements of first and second members 76, 78 are also envisioned to construct an adjustable length bridge member 75. However, the first and second members 76, 78 of the adjustable length bridge member 75 preferably are in the form of a T-beam 80 and a C-channel 82, respectively, wherein at least a portion of the T-beam 80 is slidably received within the C-channel 82. This configuration enables the T-beam 80 and C-channel 82 to move laterally with respect to one another while substantially preventing twisting and/or rotation. It is envisioned that the first and second members 76, 78 may take on other complementary shapes that enable lateral movement while in the first preferred embodiment, preferably, substantially preventing twisting and/or rotation. In use, it is envisioned that the adjustable length bridge member 75 may enable adjustment from about 30 mm to about 90 mm between spinal rod centers.

The adjustable length bridge member 75 also preferably includes a mechanism for fixing the position of the first and second members 76, 78 with respect to one another. The mechanism may be any mechanism now or hereafter known including, but not limited to, for example, a bolt, ratchet, clamp, etc. As shown, the adjustable length bridge member 75 preferably includes a translation screw 85 for generating the necessary clamping force to secure the position of the first and second members 76, 78 with respect to one another.

The translation screw 85, either alone or in combination with a feature formed on the adjustable length bridge member 75, preferably is configured so that the first and second members 76, 78 are prevented from coming apart or separating. For example, the translation screw 85 is preferably "staked" so that the translation screw 85 can not be removed from the first and second member 76, 78 and hence the first and second members 76, 78 are prohibited from separating.

The first and second members 76, 78 are preferably provided with a radius to permit the transconnector 10 to span over parts of the human anatomy such as, for example, the patient's dura, facets, lamina, spinous process, etc. Preferably, the first and second members 76, 78 have a radius of about 60 mm. Although it is envisioned that other radiuses may be used. Alternatively, the first and second members 76, 78 may be straight.

The transconnector 10 includes the pair of spinal rod engaging members 20 operatively coupled to the first and second members 76, 78 that each include a rod receiving channel 21 for receiving one of the longitudinal spinal rods 5 therein. The transconnector 10 may include a pair of articulating spinal rod engaging members 22 operatively coupled to the first and second members 76, 78, respectively, a pair of non-articulating spinal rod engaging members 24 operatively coupled to the first and second members 76, 78, respectively, or any combination thereof. For example, as best shown in FIG. 1-5, one of the first and second members 76, 78 may include a non-articulating spinal rod engaging member 24 while the other of the first and second members 76, 78 may include an articulating spinal rod engaging member 22. In use, incorporation of the articulating spinal rod engaging member 22 enables the spinal rod engaging member 20 to articulate with respect to the bridge member 75 thus enabling the spinal rod engaging member 20 to engage a pair of spinal rods 5 that are generally oriented in a non-parallel manner. Preferably, the articulating spinal rod engaging member 22 enables about plus or minus twenty-two degrees (+/−22°) of articulation in the yaw direction (for a total of forty-four degrees (44°) of motion), as best shown in FIG. 6A, while permitting plus or minus fifteen degrees (+/−15°) of articulation in the roll direction (for a total of thirty degrees (30°) of motion), as best shown in FIG. 6B. Although it is envisioned that significantly more or less articulation may be permitted.

Figure 5:
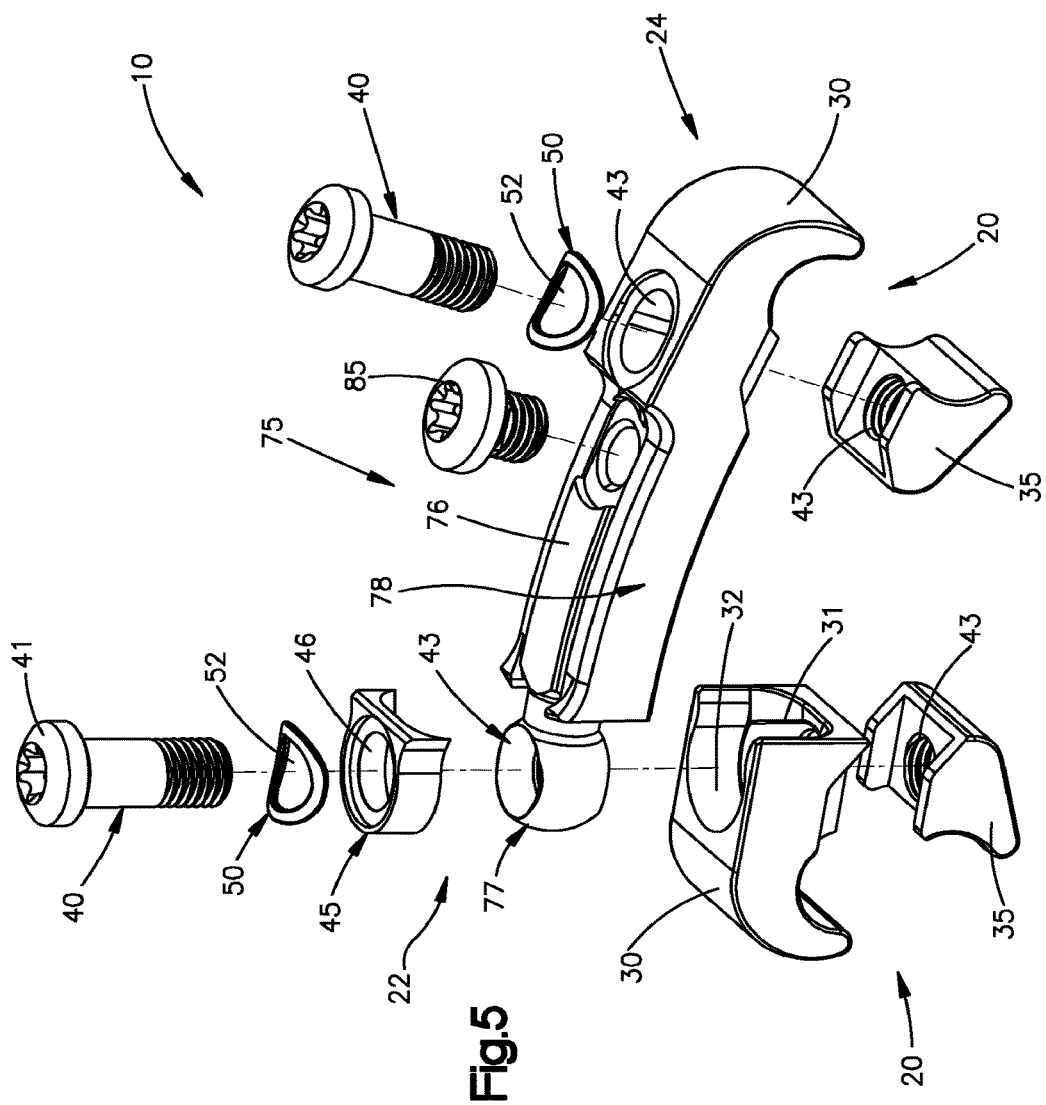
FIG. 5 illustrates a top perspective, exploded view of the transconnector of FIG. 1.
Figure 6A:
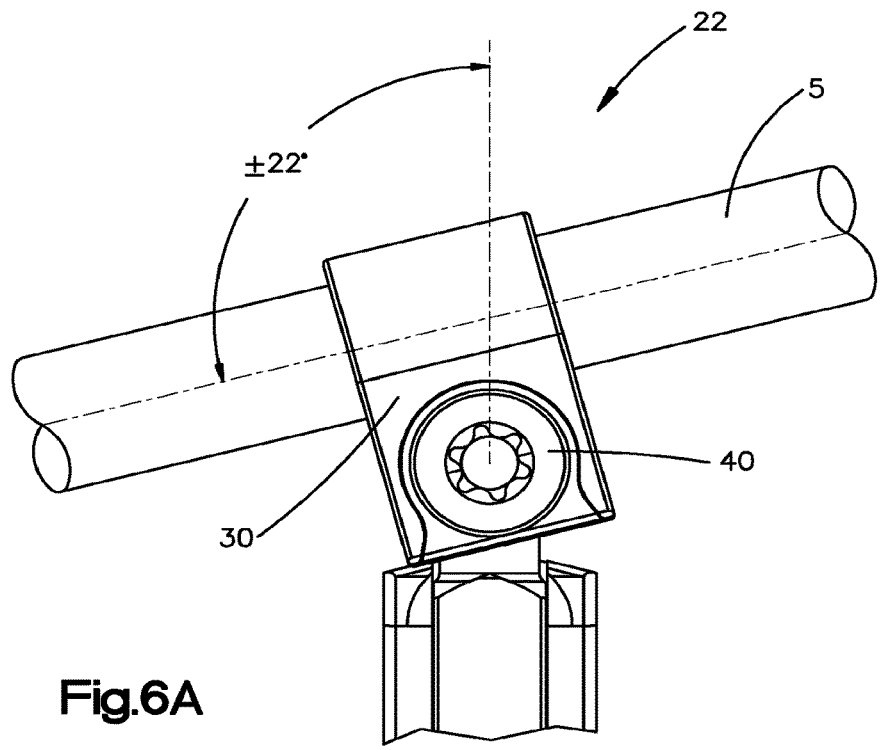
FIG. 6A illustrates a top plan view of an articulating spinal rod engaging member of the transconnector of FIG. 1, wherein the articulating spinal rod engaging member is pivoted in the yaw direction and is engaged with a spinal rod.
Figure 6B:
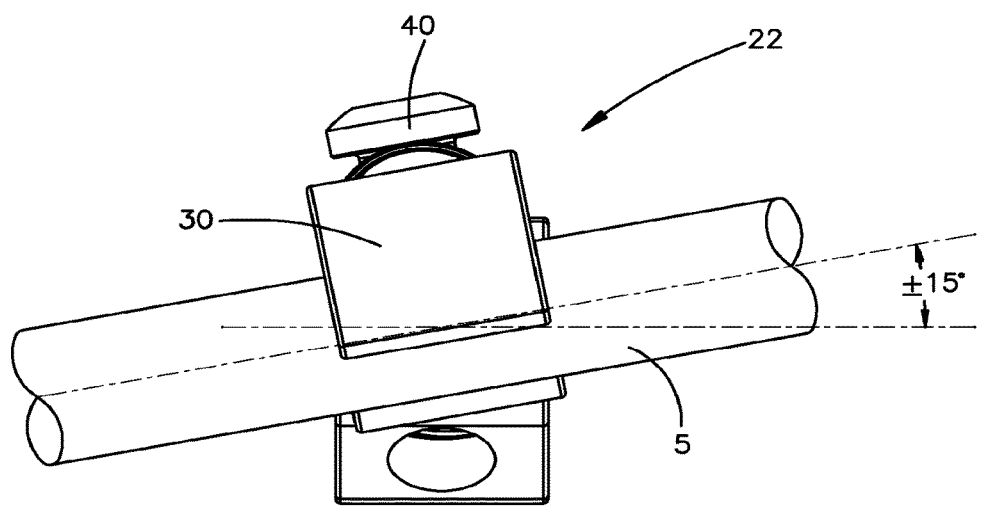
FIG. 6B illustrates a front elevational view of the articulating spinal rod engaging member of the transconnector of FIG. 1, wherein the articulating spinal rod engaging member is pivoted in the roll direction and is engaged with the spinal rod.

As best shown in FIG. 5, the articulating spinal rod engaging members 22 may include an upper clamp body 30, a lower clamp body 35, a compression cap 45 and an actuation screw 40. In the first preferred embodiment, at least one of the upper clamp bodies 30 is moveably connected to the bridge member 75 by, for example, a recess 31 formed in the upper clamp body 30, wherein the recess 31 has an inner curvate or spherical surface 32 for engaging an outer curvate or spherical surface 77 formed on at least one end of the bridge member 75 so that the upper clamp body 30 may be connected to the bridge member 75 via a curvate or spherical connecting surface. In this manner, by providing an upper clamp body 30 which is interconnected to the bridge member 75 via a curvate or spherical connecting surface, the upper clamp body 30 may articulate with respect to the bridge member 75, thus enabling the spinal rod engaging member 20 to align with a non-planar or non-parallel longitudinal spinal rods 5. The compression cap 45 preferably includes an internal curvate or spherical shape 46 for mating with the outer curvate or spherical surface 77 formed on the bridge member 75.

The lower clamp body 35 is preferably moveably connected to the upper clamp body 30 by, for example, the actuation screw 40. As shown, the bridge member 75, the upper clamp body 30, the lower clamp body 35 and the compression cap 45 preferably all include an internal bore 43 for receiving the actuation screw 40. That is, preferably, the upper clamp body 30, the lower clamp body 35, the bridge member 75 and the compression cap 45 all include a bore 43 for receiving the actuation screw 40 such that the actuation screw 40 passes through the compression cap 45, the upper clamp body 30, the bridge member 75 and into threaded engagement with the lower clamp body 35 such that rotation of the actuation screw 40 moves the lower clamp body 35 with respect to the upper clamp body 30 to thereby secure the rod 5 within the rod receiving channel 21 and compresses the internal curvate or spherical surface 46 formed in the compression cap 45 against the outer curvate or spherical surface 77 formed on the bridge member 75 to fix the position of the articulating spinal rod engaging members 22 with respect to the bridge member 75. Thus, in use, rotation of the actuation screw 40 preferably causes the lower clamp body 35 to move towards the upper clamp body 30 to thereby secure the position of the spinal rod 5 with respect to the spinal rod engaging member 20 when the spinal rod engaging member 22 is engaged with the spinal rod 5. In addition, rotation of the actuation screw 40 also secures the position of the upper and lower clamp bodies 30, 35 with respect to the bridge member 75 (e.g., to secure the roll and yaw position of articulating spinal rod engaging members 22 with respect to the bridge member 75).

By incorporating a non-integral lower clamp body 35, the spinal rod engaging members 20 and hence the transconnector 10, requires less spinal rod clearance on the anterior side of the spinal rod 5 in order to attach the spinal rod engaging members 20 to the longitudinal spinal rods 5, thereby helping the transconnector 10 to achieve a lower profile. Alternatively, the bridge member 75 may include an integrally formed lower clamp body (not shown).

In use, the actuation screws 40 preferably include a mechanism for preventing the actuation screws 40 from becoming separated from the transconnector 10. For example, the actuation screws 40 may include "staked" ends so that the actuation screws 40 are difficult to remove from the spinal rod engaging members 20 and hence the spinal rod engaging members 20 are difficult to separate from the bridge member 75.

The upper and lower clamp bodies 30, 35 preferably define the rod receiving channel 21 for receiving the longitudinal spinal rod 5. The rod receiving channel 21 may include a roughened or textured surface, for example, a glass beaded texture, radial teeth, serrations, grooves, etc. for contacting the outer surface of the longitudinal spinal rod 5 in order to limit rotational or axial slippage of the rod 5 with respect to the spinal rod engaging members 20.

The spinal rod engaging members 20 preferably also include a spring 50. Although it is envisioned that the spring 50 may take on any number of forms now or hereafter known including, for example, a helical spring, leaf spring, compression spring, flexible block, etc. In the first preferred embodiment, the spring 50 is in the form of a spring washer. The spring 50 preferably provides an opposing force to permit the spinal rod engaging members 20 to provisionally "snap" onto or otherwise provisionally engage the longitudinal spinal rods 5. That is, the spring 50 preferably includes a bore 52 for receiving the actuation screw 40 therethrough. The spring 50 is preferably located between the head 41 of the actuation screw 40 and the compression cap 45 or the integral upper clamp body 30 so that the spring 50 provides a bias force which causes the lower clamp body 35 to press against the upper clamp body 30 so that the longitudinal spinal rod 5 may be provisionally or tentatively received and held within the rod receiving channels 21 formed in the spinal rod engaging members 20. The spring 50 biases the lower clamp body 35 toward or into engagement with the upper clamp body 30 by applying a bias force to the underside of the head of the actuation screw 40, which biases the lower clamp body 35 toward the upper clamp body 30 through engagement of the threads on the actuation screw 40 and the threads in the bore 43 of the lower clamp body 30. Accordingly, in a closed position, the spring 50 biases the lower clamp body 35 toward the upper clamp body 30 to define a relatively small diameter rod receiving channel 21 in the first preferred embodiment, but also permits the lower clamp body 35 to be urged away from the upper clamp body 30 by compressing the spring 50, thereby enlarging the rod receiving channel 21 such that the rod 5 may be received therein.

As previously mentioned and as best shown in FIGS. 1-5, one or both of the spinal rod engaging members 20 may be configured as a non-articulating spinal rod engaging member 24. In use, a non-articulating spinal rod engaging member 24 is substantially identical to an articulating spinal rod engaging member 22 described above, however, in the non-articulating spinal rod engaging member 24, the upper clamp body 30 may be integrally formed with the bridge member 75 (shown as integrally formed with the second member 78 of the bridge member 75). Alternatively, it is envisioned that the upper clamp body 30 may be a separate and distinct member from the bridge member 75 and affixed thereto by any means now or hereafter known, such as welding, adhesive bonding, clamping, fastening, etc.

Moreover, in use, rotation of the actuation screw 40 preferably secures the position of the upper and lower clamp bodies 30, 35 with respect to the bridge member 75 (e.g., fixes the articulated position (i.e., yaw and roll positions) of the articulated spinal rod engaging member 22 with respect to the bridge member 75) and provides clamping force to secure the spinal rod 5 in the rod-receiving channel 21 of the articulated spinal rod engaging member 22. For a non-articulated spinal rod-engaging member 24, rotation of the actuation screw 40 preferably only provides the necessary clamping force to secure the spinal rod 5 in the rod receiving channel 21 of the spinal rod engaging member 24.

Figure 7:
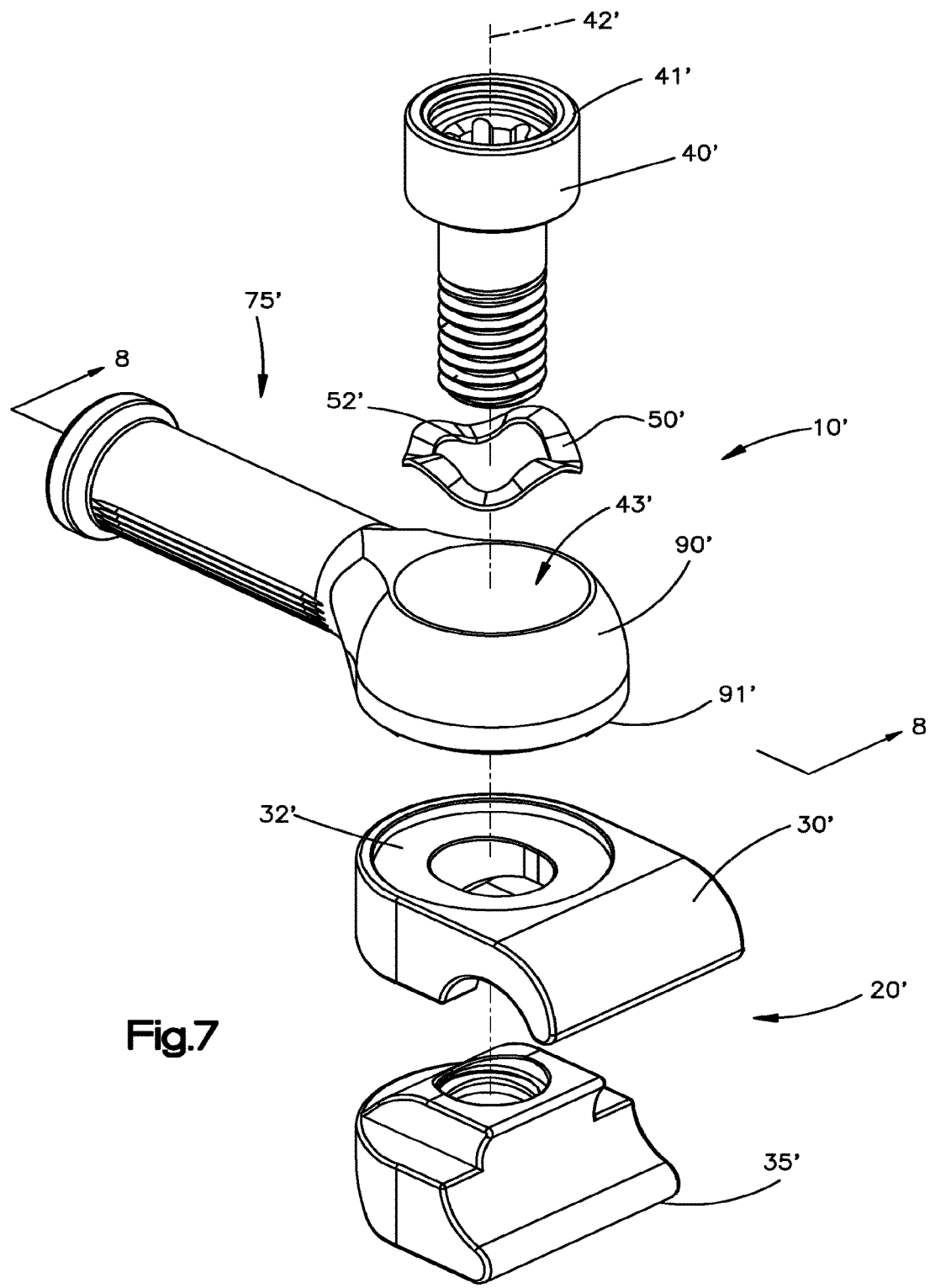
FIG. 7 illustrates a front perspective, exploded view of a transconnector in accordance with a second preferred embodiment of the present invention.
Figure 8:
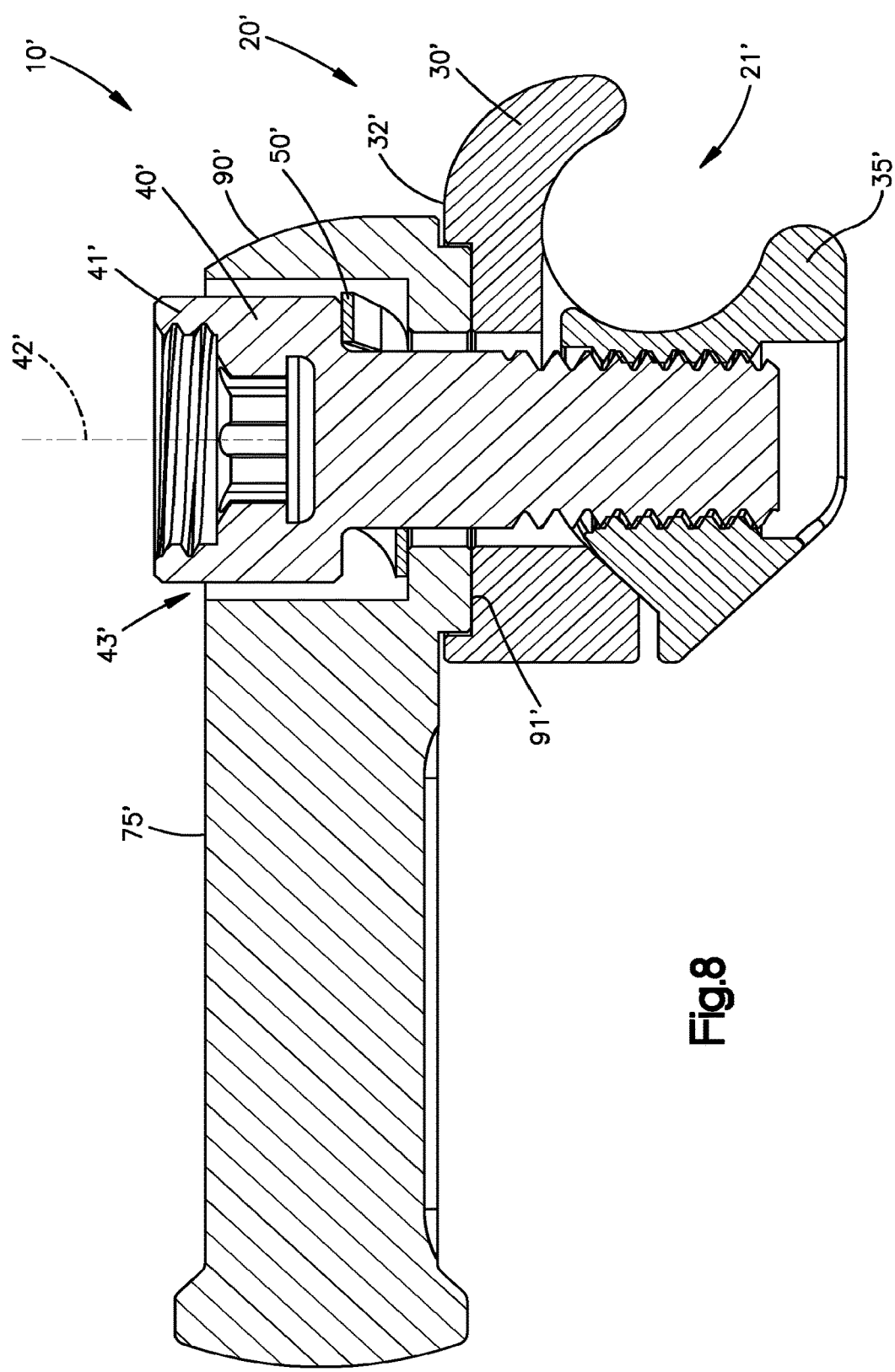
FIG. 8 illustrates a cross-sectional view of the transconnector of FIG. 7, taken along line 8-8 of FIG. 7.

Referring to FIGS. 7 and 8, in a second preferred embodiment of a transconnector 10', the bridge member 75' may be in the form of first and second telescopic, tubular members (only one of which is shown) wherein the first member is sized and configured to be received within the second member. Alternatively, as previously mentioned, the transconnector 10' may only include one spinal rod engaging member 20' for directly engaging only one spinal rod 5, while the other end of the transconnector 10' is configured to directly engage a patient's vertebra via, for example, a bone screw.

Moreover, as shown, the spinal rod engaging members 20' may be located in a stacked relationship relative to the bridge member 75'. That is, for example, the bridge member 75' may be located on top of or to one side of the upper and lower clamp bodies 30', 35'. The bridge member 75' may include an enlarged diametric end 90' having the bore 43' for receiving the actuation screw 40'. The upper and lower clamp bodies 30', 35' are preferably moveably coupled to the bridge member 75' so that the spinal rod engaging members 20' is preferably, pivotally associated with the bridge member 75' about the longitudinal axis 42' of the actuation screw 40' to better accommodate non-parallel and/or converging/diverging rods 5. The bottom surface 91' of the enlarged diametric end 90' may be configured to contact the top surface 32' of the upper clamp body 30'. The bottom surface 91' of the enlarged diametric ends 90' and the top surface 32' of the upper clamp body 30' may include corresponding serrations in order to provide better securement. Alternatively, the bottom surface 91' of the enlarged diametric ends 90' and the top surface 32' of the upper clamp body 30' may be bead blasted (e.g., roughened surface) in order to provide potentially improved securement.

The spinal rod engaging members 20' preferably also include a spring 50' to provide an opposing force in order to permit the longitudinal spinal rods 5 to provisionally snap into the rod receiving channels 21' formed in the spinal rod engaging members 20'. As previously described, the spring 50' preferably includes a bore 52' for receiving the actuation screw 40' therethrough. The spring 50' is preferably located between the head 41' of the actuation screw 40' and the bridge member 75', as best shown in FIG. 7, so that the spring 50' provides an initial force which causes the lower clamp body 35' to press against the upper clamp body 30' so that the longitudinal spinal rod 5 may be tentatively or provisionally received and held within the rod receiving channel 21'. The spring 50' may take on any number of forms now or hereafter known including, but not limited to, a spring washer. The spring 50' preferably provides an opposing force in order to permit the spinal rod engaging members 20' to provisionally snap onto the longitudinal spinal rods 5.

The operation of the transconnector 10' is substantially similar to the operation of the transconnector 10 discussed above.

Figure 9A:
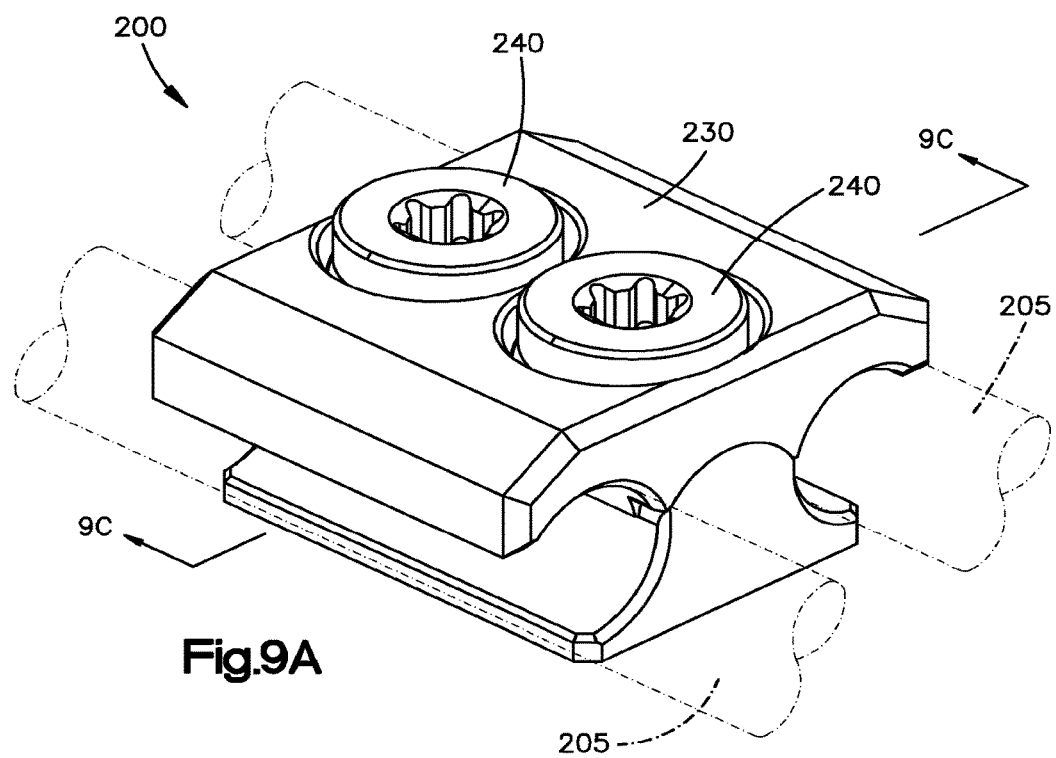
FIG. 9A illustrates a top perspective view of a coupler or transconnector mounted to spinal rods in accordance with a third preferred embodiment of the present invention.
Figure 9B:
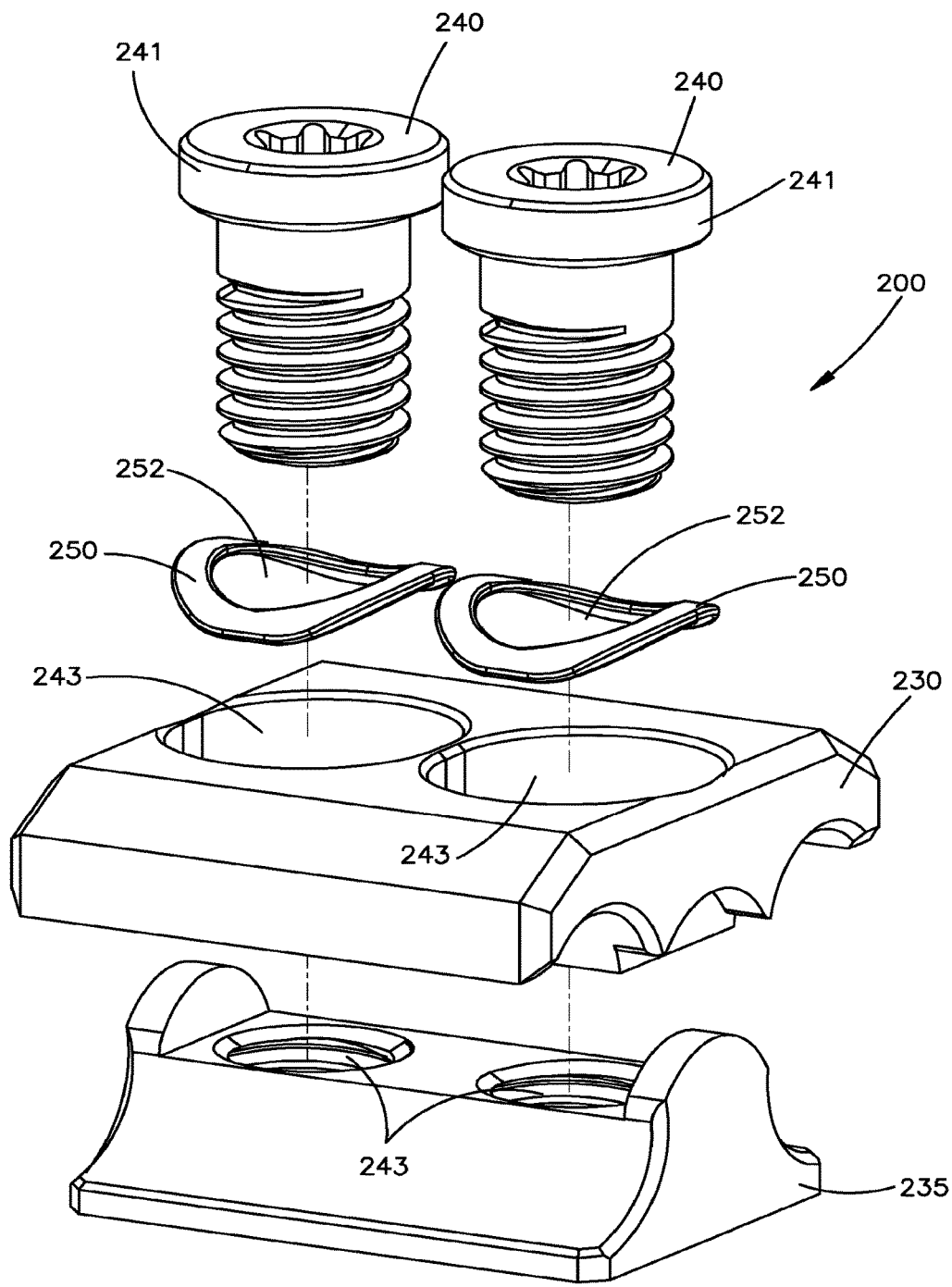
FIG. 9B illustrates an exploded view of the coupler of FIG. 9A.
Figure 9C:
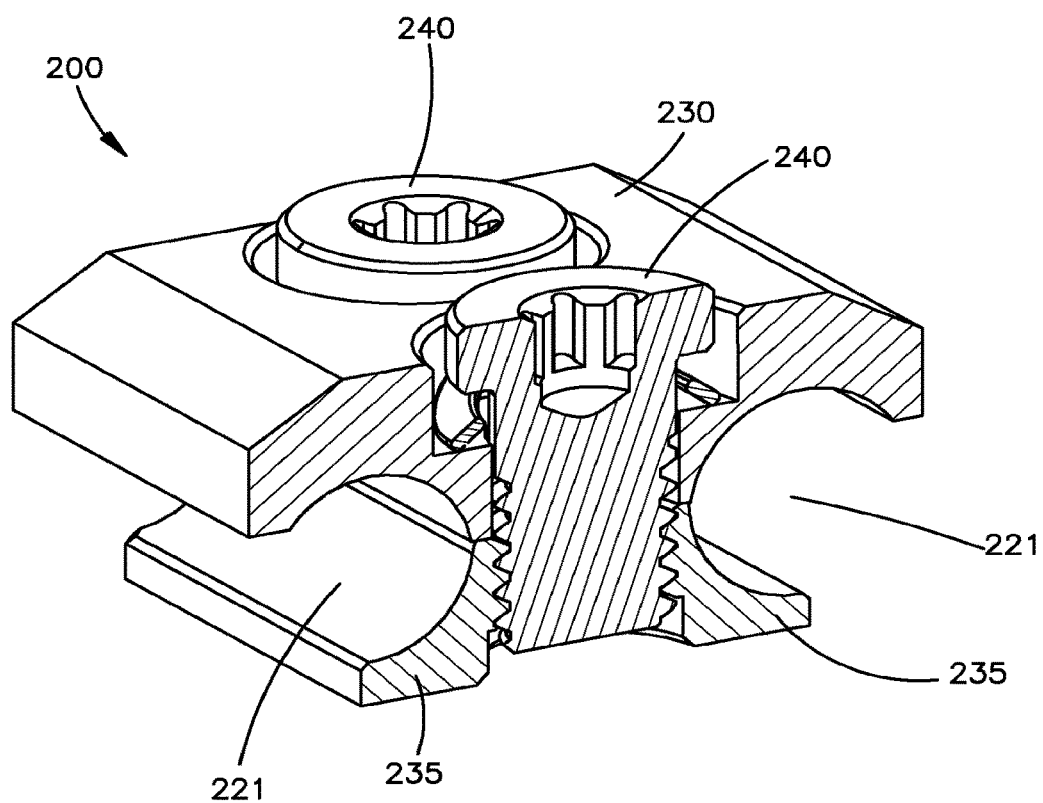
FIG. 9C illustrates a cross-section view of the coupler of FIG. 9A, taken along line 9C-9C of FIG. 9A.

Alternatively, as shown in FIGS. 9A-9C, a coupler or transconnector 200 in accordance with a third preferred embodiment for interconnecting substantially parallel rods 205 is disclosed. In use, the coupler 200 may be used as a transconnector to couple substantially parallel transverse spinal rods 5. Alternatively, the coupler 200 may be used to couple substantially parallel longitudinal spinal rods 5. Furthermore, the coupler 200 may be used in other parts of the body to couple substantially parallel rods including, but not limited to, internal or external fixation of long bones.

The coupler 200 preferably includes an upper clamp body 230, a lower clamp body 235, one or more actuation screws 240, and one or more springs 250. The operation of the coupler 200 is substantially identical to the operation of the transconnectors 10, 10' discussed above. That is, the lower clamp body 235 is preferably moveably connected to the upper clamp body 230 by, for example, the actuation screw 240. Preferably, the upper clamp body 230 and the lower clamp body 235 include an internal bore 243 that receives the actuation screw 240. The upper and lower clamp bodies 230, 235 define a rod receiving channel 221 for receiving the longitudinal spinal rods 205. In use, rotation of the actuation screw 240 causes the lower clamp body 235 to move towards the upper clamp body 230 to thereby secure the position of the spinal rods 205 with respect to the coupler 200, when the spinal rods 205 are positioned in the rod receiving channel 221.

The spring 250 preferably provides an opposing force in order to permit the longitudinal spinal rods 205 provisionally snap into the rod receiving channels 221 formed in the coupler 200. The spring 250 is preferably in the form of a spring washer having a bore 252 for receiving the actuation screw 240 therethrough. The spring 250 is preferably located between the head 241 of the actuation screw 240 and the upper clamp body 230 so that the spring 250 provides an initial force which causes the lower clamp body 235 to press against the upper clamp body 230 so that the longitudinal spinal rod 205 may be tentatively received and held within the rod receiving channel 221 formed in the coupler 200. The spring 250 may taken on any one of a number of different forms, as was described above.

Figure 10:
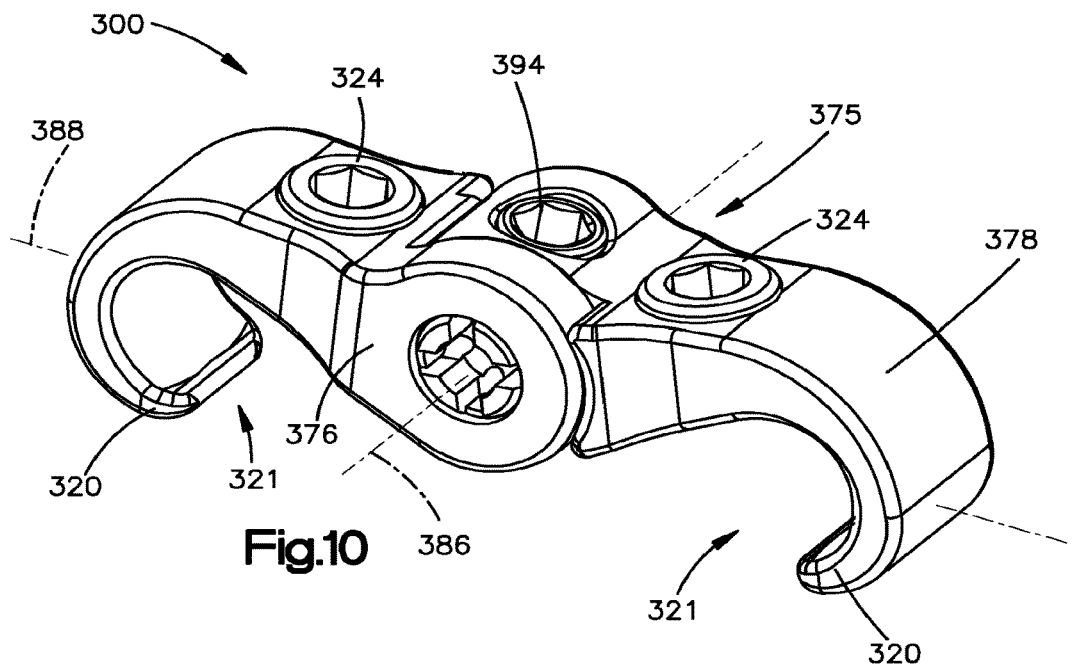
FIG. 10 illustrates a top perspective view of a transconnector in accordance with a fourth preferred embodiment of the present invention, shown in an expanded position.
Figure 10A:
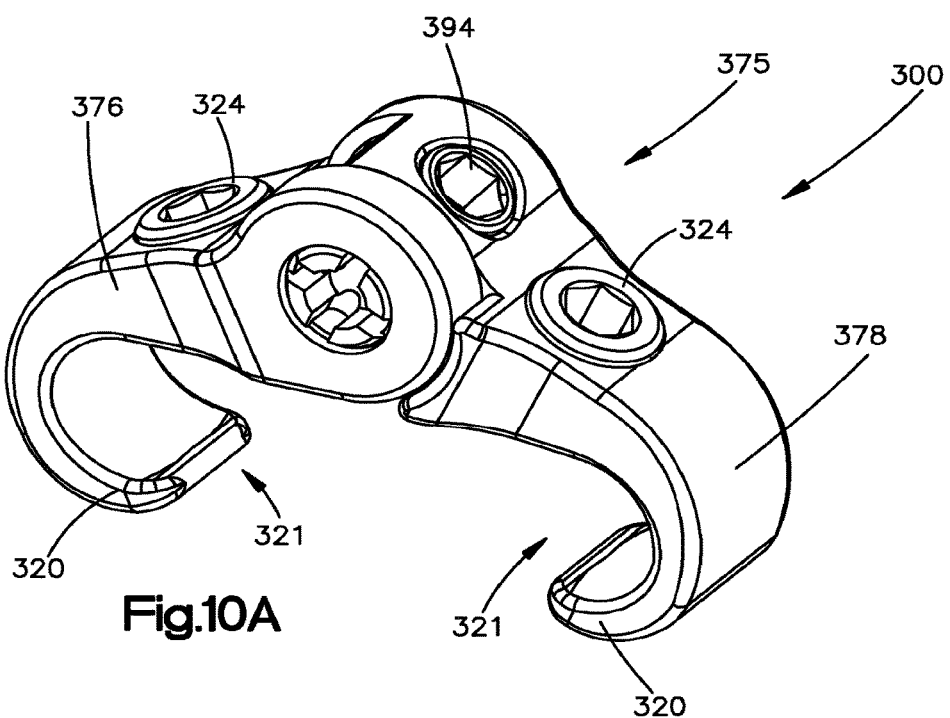
FIG. 10A illustrates a top perspective view of the transconnector of FIG. 10, shown in a partially collapsed position.
Figure 11:
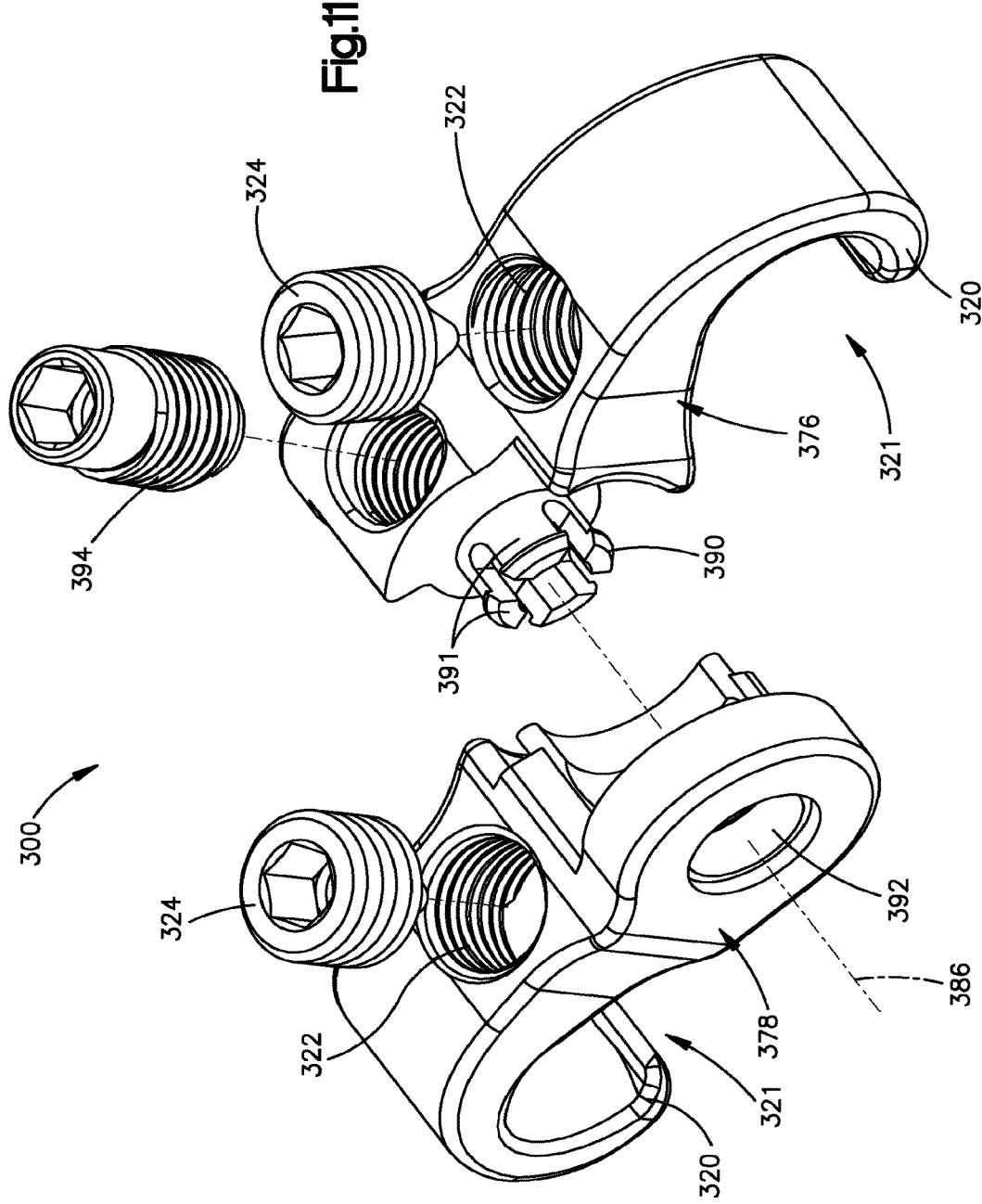
FIG. 11 illustrates an exploded view of the transconnector of FIG. 10.

A fourth preferred embodiment of a transconnector 300 is shown in FIGS. 10-11. In this fourth preferred embodiment, the bridge member 375 may be in the form of first and second members 376, 378 wherein the first member 376 is pivotally coupled or hinged to the second member 378. The first member 376 is preferably pivotally coupled or hinged to the second member 378 via a pivot axis 386 that may be substantially transverse to a longitudinal axis 388 of the transconnector 300, which is defined in an expanded position, so that pivotal adjustment of the first and second members 376, 378 causes the bridge member 375 to bend in the anatomical axial plane. In this manner, pivotable adjustment of the first member 376 with respect to the second member 378 preferably alters the length of the transconnector 300 or a distance between spinal rod engaging members 320 at either end of the transconnector 300. Pivotal adjustment of the first member 376 with respect to the second member 378 may cause the bridge member 375 to move posteriorly thus shortening the overall length of the transconnector 300, as best shown in FIG. 10A.

The first and second members 376, 378 may be coupled to one another by any means now or hereafter known that permits the first and second members 376, 378 to pivot with respect to one another. Preferably, the second member 378 includes a hole 392 formed therein, wherein the hole 392 receives a projection 390 laterally extending from the first member 376. The projection 390 preferably includes a plurality of tabs 391. The bridge member 375 preferably also includes a threaded fastener or set screw 394. The set screw 394 is threadably engageable with the first member 376 such that rotation of the set screw 394 causes the projection 390, more preferably the plurality of tabs 391 to expand, thereby causing the tabs 391 to exert a force onto the inner surface of the hole 392 to thereby secure the position of the first member 376 with respect to the second member 378.

The first and second members 376, 378 preferably include integral spinal rod engaging members 320, but are not so limited. The spinal rod engaging members 320 include a rod receiving channel 321 that receives a longitudinal spinal rod 5. The spinal rod engaging members 320 also include a throughbore 322 that receives a wedge member 324 (e.g. set screw) for securing the spinal rod 5 in the rod receiving channel 321 of the spinal rod engaging member 320. Alternatively, it is envisioned that the transconnector 300 may include non-integral spinal rod engaging members 320.

A fifth preferred embodiment of a transconnector 400 is shown in FIGS. 12 and 13. In this fifth preferred embodiment, the bridge member 475 may be in the form of first and second members 476, 478, wherein the first member 476 and the second member 478 are laterally adjustable with respect to one another. Although it is envisioned that the first and second members 476, 478 may take on any number of forms, preferably, as shown, the first and second members 476, 478 are each in the form of a non-articulating spinal rod engaging member 420 including a post 460 extending therefrom. The spinal rod engaging members 420 further include a throughbore 462 passing therethrough, wherein the throughbore 462 receives the post 460 extending from the other spinal rod engaging member 420.

The spinal rod engaging members 420 preferably include a separate, non-integral lower clamp body 435 that is moveably connected to the upper clamp body 430 by, for example, an actuation screw 440, as previously described.

In use, rotation of the actuation screw 440 preferably secures (i) the position of the lower clamp body 435 with respect to the upper clamp body 430 and hence fixes the position of the longitudinal spinal rod 5 within the rod receiving channel 421 and (ii) the position of the second member 478 with respect to the first member 476. That is, as best shown in FIG. 13, the first and second members 476, 478 preferably include a slot 464 formed therein so that rotation of the actuation screw 440 causes the spinal rod engaging members 420 to compress against the post 460 of the alternate spinal rod engaging member 420 thereby fixing the position of the first member 476 with respect to the second member 478.

As previously stated, the upper and lower clamp bodies 430, 435 preferably include a rod receiving channel 421 formed therein for receiving the longitudinal spinal rod 5. The rod receiving channel 421 may include a roughened or textured surface, for example, a glass beaded texture, radial teeth, serrations, grooves, etc. for contacting the outer surface of the longitudinal spinal rod 5 in order to prevent rotational or axial slippage of the rod 5 with respect to the spinal rod engaging members 420.

In addition, as also previously described, the upper and lower clamp bodies 430, 435 of the spinal rod engaging members 420 preferably each include a spring 450 to provide an opposing force in order to permit the spinal rod engaging members 420 to provisionally snap onto the longitudinal spinal rods 5.

The first and second members 476, 478 preferably also include a feature for preventing the first and second members 476, 478 from separating. For example, the posts 460 may include enlarged ends that limit the first and second members 476, 478 from pulling apart with respect to one another.

While the foregoing description and drawings represent the preferred embodiments of the present invention, it will be understood that various additions, modifications, combinations and/or substitutions may be made therein without departing from the spirit and scope of the present invention as defined in the accompanying claims. For example, while numerous bridge members and/or spinal rod engaging members have been described herein, it is envisioned that the different bridge members and spinal rod engaging members can be mixed and matched such that every bridge member may be configured to be used in connection with each and every spinal rod engaging member. In particular, it will be apparent to those skilled in the art that the invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components, which are particularly adapted to specific environments and operative requirements without departing from the principles of the invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed:

1. A transconnector configured to interconnect a first spinal rod and a second spinal rod; the transconnector comprising:

a first member having a first end and a second member having a second end, the first member and the second member defining a length measured from the first end to the second end, the first member being translatable relative to the second member so that the length is adjustable;

a first rod engaging member coupled to the first member, the first rod engaging member including a first upper clamp body and a first lower clamp body, the first upper clamp body including a first inner surface, the first rod engaging member further including a first rod receiving channel defined partially by the first inner surface, wherein the first rod engaging member is configured such that the first lower clamp body is movable in a first direction with respect to the first upper clamp body to secure the first spinal rod within the first rod receiving channel, the first rod engaging member defining a first location positioned on the first inner surface such that no other location on the first inner surface is spaced from the first location in the first direction; and a second rod engaging member coupled to the second member, the second rod engaging member including a second upper clamp body and a second lower clamp body, the second upper clamp body including a second inner surface, the second rod engaging member further including a second rod receiving channel defined partially by the second inner surface, wherein the second rod engaging member is configured such that the second lower clamp body is movable in a second direction with respect to the second upper clamp body to secure the second spinal rod within the second rod receiving channel, the second rod engaging member defining a second location positioned on the second inner surface such that no other location on the second inner surface is spaced from the second location in the second direction, wherein the transconnector defines a gap between a straight line from the first location to the second location and both the first member and the second member.

2. The transconnector of claim 1, further comprising a mechanism configured to fix the length such that the first member is not translatable with respect to the second member.

3. The transconnector of claim 2, wherein the mechanism is a screw configured to be inserted through one of the first and second members and into the other of the first and second members in a third direction.

4. The transconnector of claim 3, wherein when the screw is inserted through one of the first and second members and into the other of the first and second members a portion of the gap is aligned with the screw with respect to the third direction.

5. The transconnector of claim 3, wherein the screw is rotatable about an axis as the screw is inserted through one of the first and second members and into the other of the first and second members, the axis is parallel to the third direction, and a portion of the gap is aligned with the axis with respect to the third direction.

6. The transconnector of claim 1, wherein the first rod engaging member includes a spring configured to bias the first lower clamp body toward the first upper clamp body so that the first rod engaging member is configured to provisionally snap onto the first spinal rod as the first spinal rod is inserted into the first rod receiving channel.

7. The transconnector of claim 1, wherein the first rod engaging member is configured to articulate in a yaw direction and in a roll direction with respect to the first end.

8. The transconnector of claim 1, wherein the first rod engaging member includes an actuation screw, the first member defines a bore configured to receive the actuation screw such that the actuation screw passes through the bore and also passes through the first rod engaging member such that rotation of the actuation screw both secures the first spinal rod within the first rod receiving channel and secures a position of the first rod engaging member with respect to the first member.

9. A method of connecting a transconnector to both a first spinal rod and a second spinal rod, the transconnector including a first member having a first end and a second member having a second end, a first rod engaging member coupled to the first end, and a second rod engaging member coupled to the second end, the method comprising the steps of:
  positioning a portion of the first spinal rod within a first rod receiving channel of the first rod engaging member, the first rod engaging member including a first upper clamp body and a first lower clamp body that cooperate to define the first rod receiving channel;
  moving the first lower clamp body relative to the first upper clamp body in a first direction until a first surface of the first upper clamp body abuts the first spinal rod and until the first spinal rod is secured within the first rod receiving channel, the first rod engaging member defining a first location positioned on the first surface such that no other location on the first surface is spaced from the first location in the first direction;
  adjusting a length of the transconnector measured from the first end to the second end;
  positioning a portion of the second spinal rod within a second rod receiving channel of the second rod engaging member, the second rod engaging member including a second upper clamp body and a second lower clamp body that cooperate to define the second rod receiving channel;
  moving the second lower clamp body relative to the second upper clamp body until a second surface of the second upper clamp body abuts the second spinal rod and until the second spinal rod is secured within the second rod receiving channel, the second rod engaging member defining a second location positioned on the second surface such that no other location on the second surface is spaced from the second location in the second direction; and
  fixing the length of the transconnector such that a gap is defined between a straight line from the first location to the second location and the both the first member and the second member.

10. The method of claim 9, wherein the adjusting step includes the step of moving the first member relative to the second member.

11. The method of claim 10, wherein the fixing step includes the step of inserting a fixation mechanism through one of the first member and the second member, and into the other of the first member and the second member.

12. The method of claim 11, wherein the inserting step includes moving the fixation mechanism in a third direction, and a portion of the gap is aligned with the fixation mechanism in the third direction.

13. The method of claim 12, wherein the fixation mechanism is a fixation screw, and the inserting step includes the step of rotating the fixation screw about an axis that is parallel to the third direction, and a portion of the gap is aligned with the axis in the third direction.

14. The method of claim 9, wherein the step of positioning a portion of the first spinal rod includes the step of compressing a spring of the first rod engaging member, the spring configured to bias the first lower clamp body toward the first upper clamp body.

15. The method of claim 9, wherein the step of moving the first lower clamp body includes the step of compressing a spring of the first rod engaging member, the spring configured to bias the first lower clamp body toward the first upper clamp body.

16. The method of claim 9, further comprising the step of articulating the first rod engaging member in at least one of a yaw direction and a roll direction with respect to the first member.

17. The method of claim 9, wherein the step of moving the first lower clamp body includes the step of securing a position of the first rod engaging member with respect to the first member.

18. The method of claim 17, wherein the step of moving the first lower clamp body includes the step of rotating a screw, and the step of rotating a screw both secures the first spinal rod within the first rod receiving channel and secures the position of the first rod engaging member with respect to the first member.

19. The method of claim 18, wherein the step of rotating the screw simultaneously secures the first spinal rod within the first rod receiving channel and secures the position of the first rod engaging member with respect to the first member.

* * * * *